(12) United States Patent
Salamone

(10) Patent No.: US 10,456,301 B2
(45) Date of Patent: Oct. 29, 2019

(54) THERMAL REFLECTIVE LAYER FOR A WOUND CARE DRESSING

(71) Applicant: Healthko, LLC, Boca Raton, FL (US)

(72) Inventor: Jeanine M. Salamone, Boca Raton, FL (US)

(73) Assignee: HEALTHKO, LLC, Boca Raton, FL (US)

( * ) Notice: Subject to any disclaimer, the term of this patent is extended or adjusted under 35 U.S.C. 154(b) by 561 days.

(21) Appl. No.: 15/228,863

(22) Filed: Aug. 4, 2016

(65) Prior Publication Data

US 2017/0042741 A1    Feb. 16, 2017

Related U.S. Application Data

(60) Provisional application No. 62/205,316, filed on Aug. 14, 2015.

(51) Int. Cl.
*A61F 13/02* (2006.01)
*A61F 13/00* (2006.01)

(52) U.S. Cl.
CPC ...... *A61F 13/0226* (2013.01); *A61F 13/0209* (2013.01); *A61F 13/0269* (2013.01); *A61F 13/0289* (2013.01); *A61F 2013/00212* (2013.01)

(58) Field of Classification Search
CPC .. A61F 2013/00519; A61F 2013/00157; A61F 2013/00936; A61F 2013/00187; A61F 2013/00191; A61F 2013/002; A61F 2013/00204; A61F 2013/00212; A61F 7/02; A61F 13/0226; A61F 13/0209; A61F 13/0269; A61F 13/0289

See application file for complete search history.

(56) References Cited

U.S. PATENT DOCUMENTS

| | | | |
|---|---|---|---|
| 2,577,945 A | 12/1951 | Atherton | |
| 4,454,874 A * | 6/1984 | Monnier | ................ A61F 13/04 602/8 |
| 4,736,088 A * | 4/1988 | Bart | ....................... A61F 7/007 219/211 |
| 4,753,241 A * | 6/1988 | Brannigan | ............... A61F 7/02 156/210 |

(Continued)

*Primary Examiner* — Kari K Rodriquez
(74) *Attorney, Agent, or Firm* — Morse, Barnes-Brown & Pendleton, P.C.; Sean D. Detweiler, Esq.

(57) ABSTRACT

A thermal reflective layer provided either separately or in combination with a wound dressing is provided. The wound dressing typically includes a top layer, and a bottom layer on an opposite side of the wound dressing from the top layer. The thermal reflective layer is positioned between the top and bottom layers and is formed of a plurality of thermal reflecting domes arranged in an array configuration with apexes of each dome oriented toward the bottom layer of the wound dressing facing the wound upon which the wound dressing is configured for placement. This configuration reflects body heat back on to the wound when the wound dressing is in place, and more rapidly increases the wound surface to a physiologically optimum healing temperature more rapidly than other conventional wound dressings, which improves the facilitation of wound healing. The configuration also enables wound visualization, and required wound piercing procedures.

19 Claims, 5 Drawing Sheets

(56) References Cited

U.S. PATENT DOCUMENTS

| | | | | |
|---|---|---|---|---|
| 5,531,670 | A | * | 7/1996 | Westby ............... A61F 7/02 602/41 |
| 5,585,154 | A | * | 12/1996 | Rhoades ............ B32B 3/12 428/35.9 |
| 6,613,953 | B1 | * | 9/2003 | Altura ................ A61F 7/02 602/41 |
| 8,530,720 | B2 | | 9/2013 | Freer et al. |
| 2002/0115972 | A1 | * | 8/2002 | Dabi ............... A61F 13/0203 604/383 |
| 2003/0036716 | A1 | * | 2/2003 | Knutson .......... A61F 15/008 602/43 |
| 2003/0144619 | A1 | * | 7/2003 | Augustine ........ A61F 7/007 602/2 |
| 2008/0177253 | A1 | * | 7/2008 | Boehringer ..... A61F 13/00021 604/543 |
| 2011/0230848 | A1 | * | 9/2011 | Manwaring ...... A61M 1/0088 604/290 |
| 2011/0264175 | A1 | * | 10/2011 | Barsky .............. A61F 7/007 607/90 |
| 2013/0030341 | A1 | * | 1/2013 | Freer ............... A61F 13/0233 602/43 |

* cited by examiner

THERMAL REFLECTIVE LAYER FOR A WOUND CARE DRESSING

CROSS-REFERENCE TO RELATED APPLICATION(S)

This application claims priority to, and the benefit of, U.S. Provisional Application No. 62/205,316, filed Aug. 14, 2015, for all subject matter common to both applications. The disclosure of said provisional application is hereby incorporated herein by reference in its entirety.

FIELD OF THE INVENTION

The present invention relates to wound care dressings suitable for facilitating faster wound healing. In particular, the present invention relates to a wound care dressing configuration that quickly achieves and maintains a wound at an optimum wound healing temperature when placed over a wound, due to inclusion of a thermal reflective layer.

BACKGROUND

Conventional devices, systems, methods, and processes pursue various approaches in an attempt to achieve optimum wound healing environments. The process of wound healing is complex and fragile. There are many different factors involved, including mechanical stress on the wound, debris in the wound, temperature of the wound, desiccation and maceration, infection, chemical stress, medications, and other physiological characteristics of the patient. Primary wound dressings include topical agents placed directly on the wound, while secondary wound dressings include dressings that cover the primary dressings and the wound bed.

One factor noted in the healing process is the temperature at which the wound undergoes optimal healing. It is believed that temperature controls the rate of chemical and enzymatic processes occurring within the wound, as well as the metabolism of cells and tissue engaged in the repair process.

Frequent dressing changes or wound cleansing with room temperature solutions to address the factors of debris, infection, and the like, also have the negative effect of reducing wound temperature. Whenever a conventional secondary wound dressing (such as bordered gauze) is changed, the wound bed is cooled with removal of the old dressing and with cleansing/irrigation of the wound bed. The molecular level body cells involved in the healing process (e.g., fibroblast, keratinocytes, cytokines, proteases, growth factor activity) slow down or halt function when their environment falls far below body temperature. Thus, wound dressings that promote a "cooling" effect may not support wound repair, and the process of replacing wound dressings promotes a cooling effect that also does not support wound repair.

There are conventional dressings that attempt to increase the wound temperature faster than bordered gauzes, once the dressing is in place. A bordered foam dressing provides more thermoregulation than bordered gauze. The foam brings the wound bed to optimal wound healing temperature faster, but there are negatives to the foam. Foam holds more wound drainage or other bodily excretions and therefore can keep the wound bed moist and potentially expose the wound to undesirable bacteria and the like. Some moisture is good at the wound bed, but too much moisture can make a wound deteriorate (and macerate the periwound tissue). In addition, prior attempts at dressings that promoted more rapid temperature increases of the wound included placing a metal foil sheet over the wound. While this had the desired effect of more rapidly increasing wound temperature relative to bordered gauzes, a shortcoming of this type of configuration is that wound drainage is hindered by the liquid impermeable foil, the opaque foil prevents observation of the wound through the dressing, prevents observation of saturation levels of any dressing wound contact surfaces that absorb wound exudates, and procedures such as strike through wound drainage cannot be visualized, thus hindering the implementation of such procedures.

SUMMARY

There is a need for a wound dressing configuration that increases the wound temperature to normal body temperature more rapidly than conventional bordered gauze or bordered foam dressings, while enabling observation of wound characteristics and performance of wound piercing procedures. The present invention is directed toward further solutions to address this need, in addition to having other desirable characteristics. Specifically, the present invention includes a wound dressing configuration including a thermal reflective layer formed of a plurality of thermal reflective domes arranged in an array pattern with interstitial gaps therebetween enabling visualization of the underlying wound for purposes of observing wound drainage, visualization of dressing saturation levels, and the like, as well as enabling performance of strike through wound drainage or other similar procedures. The thermal reflective layer reflects body heat back toward the wound, thereby increasing wound temperature to the body temperature of the patient at a faster rate than conventional bordered dressings.

In accordance with an example embodiment of the present invention, a wound dressing includes a top layer. A bottom layer on an opposite side of the wound dressing from the top layer includes a wound contact layer having a wound facing surface. A thermal reflective layer includes a plurality of thermal reflecting domes arranged in an array configuration with apexes of each dome of the plurality of thermal reflecting domes oriented toward the bottom layer of the wound dressing.

In accordance with aspects of the present invention, the thermal reflective layer is passive and does not itself generate heat. Each dome of the plurality of thermal reflecting domes can have a hemispherical geometry. Each dome of the plurality of thermal reflecting domes can have a focal length to diameter ratio of between about 0.25 and about 0.5. Each dome of the plurality of thermal reflecting domes can have a diameter of no greater than about 4 mm. Each dome of the plurality of thermal reflecting domes can include a polymer structure with a reflective coating. The polymer structure can be a structure of polyethylene terephthalate (PET) or polyvinyl chloride (PVC). The reflective coating can include a metallic layer. The reflective coating can include an aluminum vacuum vapor deposition reflective layer.

In accordance with aspects of the present invention, the wound dressing can further include a plurality of interstitial gaps between each dome of the plurality of thermal reflecting domes. The plurality of interstitial gaps can be made of needle permeable material.

In accordance with aspects of the present invention, the wound dressing can be flexible and compliant to a wound surface upon which it is placed. The wound dressing can be sterile. The bottom layer can include a gauze, a super-absorbent material, a composite material, or a foam. The top layer can include an adhesive layer suitable for adhering the wound dressing to a skin surface of a patient. The adhesive layer can include a tape selected from the group consisting of transparent adhesive film, paper tape, pink tape, fabric tape, and adhesive bandage. The top layer can include a non-adhesive wrap layer. The plurality of thermal reflecting domes can be affixed to the top layer. The plurality of thermal reflecting domes can be affixed to a base layer, which can be disposed between the top layer and the bottom layer of the wound dressing.

In accordance with an example embodiment of the present invention, a method of making a wound dressing includes providing a plurality of thermal reflecting domes arranged in an array configuration on a top layer to form a thermal reflective layer. The thermal reflective layer is combined with a bottom layer comprising a wound contact layer having a wound facing surface to form the wound dressing. Apexes of each dome of the plurality of thermal reflecting domes are oriented toward the bottom layer.

In accordance with an example embodiment of the present invention, a wound dressing thermal reflective layer includes a base layer with a plurality of thermal reflecting domes arranged thereon in an array configuration with apexes of each dome of the plurality of thermal reflecting domes oriented toward an opposite direction from the base layer. The thermal reflective layer is suitable for incorporation into a wound dressing as a layer of the wound dressing.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1A:
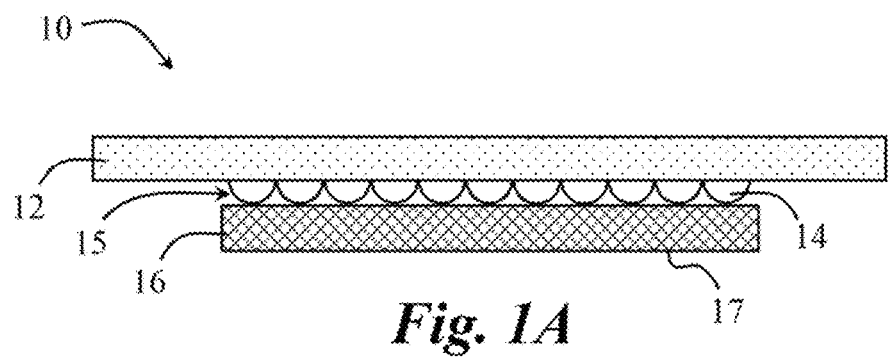
FIG. 1A is a side cross-sectional view of a wound dressing, in accordance with one embodiment of the present invention.

An illustrative embodiment of the present invention relates to a thermal reflective layer provided either separately or in combination with a wound dressing. The wound dressing typically includes a top layer, and a bottom layer on an opposite side of the wound dressing from the top layer, the bottom layer formed of a wound contact layer. The thermal reflective layer is positioned between the top and bottom layers and is formed of a plurality of thermal reflecting domes arranged in an array configuration with apexes of each dome of the plurality of thermal reflecting domes oriented toward the bottom layer of the wound dressing. This configuration has been determined by the inventor to reflect body heat back on to a wound when the wound dressing is in place, and more rapidly increase the wound surface to a physiologically optimum healing temperature more rapidly than other conventional wound dressings. By more rapidly increasing the wound surface temperature to the optimum healing temperature (i.e., at or close to body temperature), the amount of time the wound has a lower temperature where healing does not occur (or does not occur as well) is decreased or kept to a minimum. Accordingly, the wound is able to heal better and faster versus conventional wound dressings that do not incorporate the thermal layer configuration of the present invention. The configuration also enables wound visualization, observation of wound exudates, and required wound piercing procedures.

FIGS. 1A through 6, wherein like parts are designated by like reference numerals throughout, illustrate an example embodiment or embodiments of a thermal reflective layer of a wound dressing, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Turning to FIG. 1A, a side view cross-section of a wound dressing 10 is shown. The wound dressing 10 includes a top layer 12, a plurality of thermal reflecting domes 14, and a bottom layer 16. The bottom layer 16 is disposed on an opposite side of the wound dressing 10 from the top layer 12. The bottom layer 16 is formed of a wound contact layer having a wound facing surface 17. The plurality of thermal reflecting domes 14 form a thermal reflective layer 15 in that they are arranged in an array configuration with apexes of each dome of the plurality of thermal reflecting domes 14 oriented toward the bottom layer 16 of the wound dressing 10, as shown in the figures. The number of reflecting domes in each column and row of the array can vary, depending on the dimensions of each reflecting dome of the plurality of thermal reflecting domes 14, and the desired size of the final array that is to be incorporated into the wound dressing 10. A more common range for conventional sized wound dressings 10 is 4 in.×4 in. overall dimension with a 2 in.×2 in. gauze or foam making up the bottom layer 16. Another common size for bordered dressings is a 6 in.×6 in. overall dimension with a 4 in.×4 in. bottom gauze or foam making up the bottom layer 16. Likewise, the wound dressings 10 are also conventionally square or rectangular shaped, in similar ranges of length and width. Accordingly, it is anticipated that the array of the plurality of thermal reflecting domes 14 will have a quantity of domes that fit within wound dressings 10 having conventional or desired overall dimensions, as would be appreciated by those of skill in the art.

The thermal reflective layer 15 formed of the plurality of thermal reflecting domes 14 is passive and does not itself generate heat. That is, there are no heating elements or other sources of heat contained in the thermal reflective layer 15. Rather, the plurality of thermal reflecting domes 14 are configured to reflect back heat that is generated by, e.g., a wound surface 24 (see FIG. 6) against which the wound dressing 10 is placed. As such, the patient's body is the source of heat, and the thermal reflective layer 15 is configured to efficiently and effectively reflect back the heat of the patient's body in the manner described herein.

Each dome of the plurality of thermal reflecting domes 14 can have a hemispherical geometry. Likewise, each dome of the plurality of thermal reflecting domes 14 can have a geometry that is about or approaching hemispherical, but is not as mathematically precise as a half-sphere, i.e., generally hemispherical. More importantly is the generally hemispherical dome-like convex configuration that serves to more efficiently reflect heat back to the wound surface 24 relative to the reflectivity of a flat sheet of reflective material. The apex or generally center point of the curved surface portion of the thermal reflecting is oriented generally toward the bottom layer 16 of the wound dressing 10, which means that the apex is oriented generally in the direction of the wound surface 24 against which the wound dressing 10 is placed when in use. As such, it is the curved convex side of the plurality of thermal reflecting domes 14 that creates the reflective characteristics of the thermal reflective layer 15, and not the flat sides of the domes, which are used for affixing the plurality of thermal reflecting domes 14 in place.

In accordance with example embodiments of the present invention, each dome of the plurality of thermal reflecting domes 14 has a focal length to diameter ratio of between about 0.25 and about 0.5. Each dome of the plurality of thermal reflecting domes 14 has a diameter of no greater than about 4 mm in a preferred configuration. Smaller diameter domes can also be utilized, but were not found to be substantially more reflective than domes having a 4 mm diameter. Likewise, larger diameter domes can also be used, but were also not found to be substantially more reflective than domes having a 4 mm diameter. As such, the preferred dimension is about a 4 mm, or less, diameter for each dome (e.g., including but not limited to 1 mm, 2 mm, or 3 mm as well). Each dome of the plurality of thermal reflecting domes 14 can be formed of a polymer structure with a reflective coating. The polymer structure can be, for example, a structure of polyethylene terephthalate (PET) or polyvinyl chloride (PVC). The reflective coating can be a metallic layer, such as for example, an aluminum vacuum vapor deposition reflective layer, the formation of which onto a PET or PVC base is readily understood by those of skill in the art. Each dome of the plurality of thermal reflecting domes 14 is made of materials that are compatible and safe for use in conjunction with patient skin in the manner described herein, as would be readily understood by those of skill in the art.

Figure 1B:
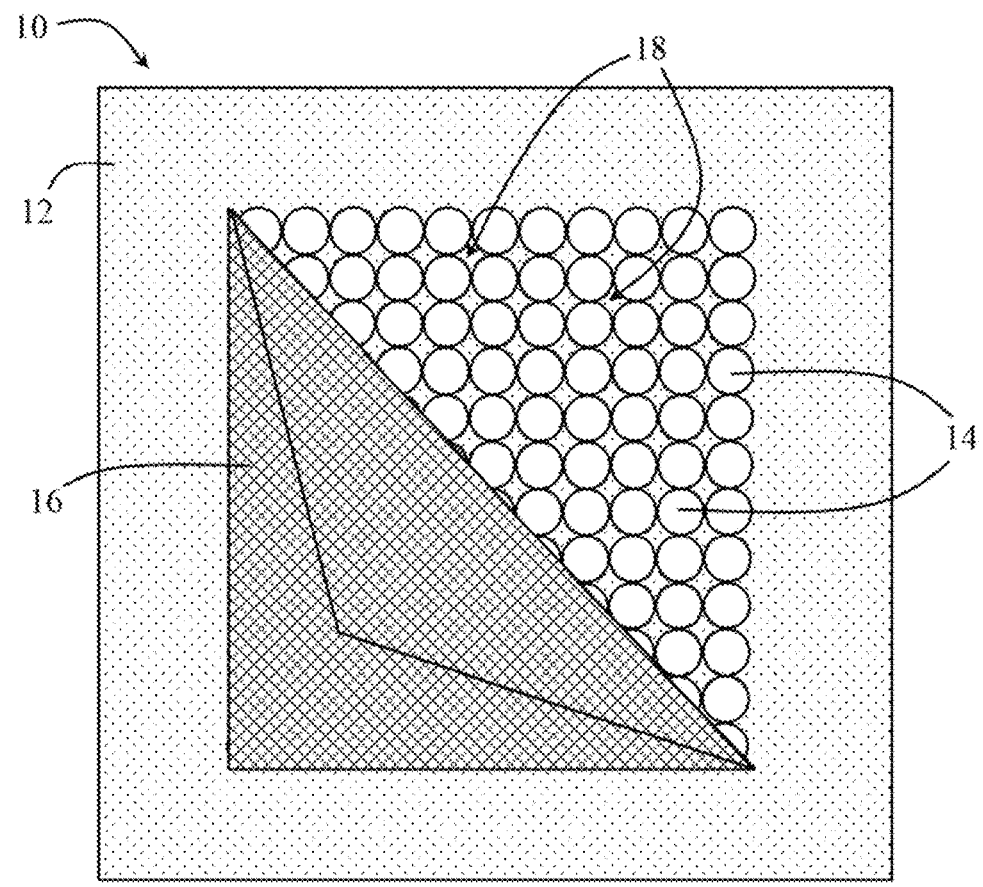
FIG. 1B is a bottom plan view of the wound dressing of FIG. 1A, with a bottom layer peeled partially away to reveal a thermal reflective layer for illustrative purposes, in accordance with the present invention.

In accordance with example embodiments of the present invention, a plurality of interstitial gaps 18 are disposed between each of the domes of the plurality of thermal reflecting domes 14 (see FIG. 1B). The interstitial gaps 18 enable several features and characteristics of the wound dressing 10. Specifically, the interstitial gaps 18 provide areas that are to a degree translucent, such that depending on the material of the top layer 12 and the bottom layer 16, it is possible to see through the thermal reflective layer 15 to the wound surface 24 to view wound draining occurrences, or the like. That is, the plurality of thermal reflecting domes 14 are not translucent; they are opaque, which is a common characteristic of materials or structures having a thermally reflective surface. As such, it is not possible to see through the thermal reflecting domes 14 themselves to any degree that would allow viewing of wound draining occurrences. Such would also be the case with an opaque thermal reflective layer that is sheet-like, which would prevent all viewing through the wound dressing 10 from a top layer 12 through to a bottom layer 16 to view wound drainage occurrences. Furthermore, the interstitial gaps 18 of the present invention can be formed of needle permeable material. By "needle permeable" what is meant is the a clinician or other skilled person may easily perforate through the material, without damaging disruption, using a conventional needle as would be typically used in medical-related procedures, as would be readily appreciated by those of skill in the art. Accordingly, it is possible with the wound dressing 10 of the present invention to use a needle to pass through the interstitial gaps 18 to the wound surface 24, and perform wound piercing or probing procedures.

The plurality of thermal reflecting domes 14 having interstitial gaps 18 therebetween also contribute to the wound dressing 10 being flexible and compliant to a wound surface 24 upon which it is placed. That is, in accordance with example embodiments of the present invention, the wound dressing 10 is not a rigid plate or other structure. Rather, as the wound dressing 10 is laid upon a wound surface 24 of a patient, the interstitial gaps 18 allow the wound dressing 10 to flex and comply with the underlying wound surface 24. The bottom layer 16 can be formed of a material that is safe for placement against patient skin, such as a gauze, a super-absorbent dressing material, a composite material, or a foam, as example materials readily understood by those of skill in the art. Such materials forming the bottom layer 16 contribute to the wound dressing 10 being a flexible and wound compliant wound dressing 10. Likewise, the top layer 12 can be formed of a flexible material. In accordance with some example embodiments, the top layer 12 can be an adhesive layer suitable for adhering the wound dressing 10 to a skin surface of a patient with an adhesive that is safe for use on patient skin. Such adhesive layers are known to those of skill in the art, and therefore do not require further elaboration here. For example, such adhesive layers can include, but are not limited to, a tape, such as a transparent adhesive film, paper tape, pink tape, fabric tape, and/or an adhesive bandage. In accordance with some example embodiments, the top layer 12 is formed of a non-adhesive wrap layer, as would be readily appreciated by those of skill in the art.

Figure 5:
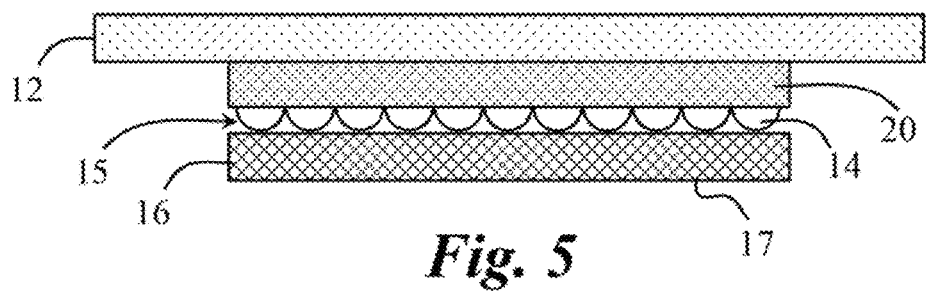
FIG. 5 is a side cross-sectional view of a wound dressing, in according with one embodiment of the present invention.
Figure 6:
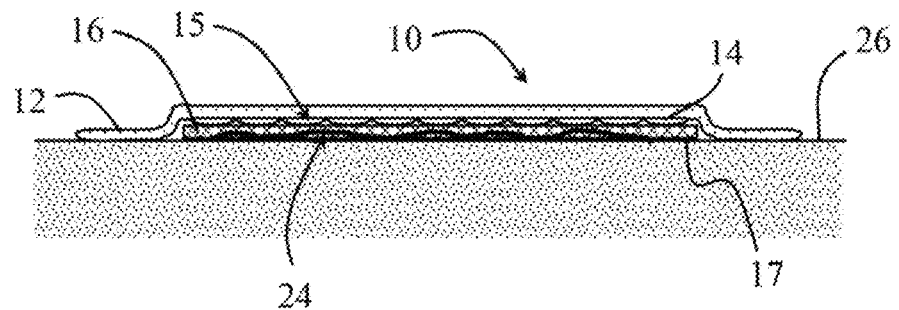
FIG. 6 is a side cross-sectional view of a wound dressing adhered to a patient, in accordance with aspects of the present invention.

In accordance with an example embodiment of the present invention, the plurality of thermal reflecting domes 14 can be affixed to the top layer 12, either using the adhesive inherent in the top layer 12 (if it is an adhesive layer), or through use of an additional medically compliant adhesive, such as would be readily understood by those of skill in the art. Alternatively, the plurality of thermal reflecting domes 14 can be affixed to a base layer 20, with a primary function of holding the plurality of thermal reflecting domes 14 in the array configuration, and which can then be disposed between the top layer 12 and the bottom layer 16, as depicted in FIG. 5.

In accordance with aspects of the present invention, the wound dressing 10 is sterile. The wound dressing 10 may be manufactured as a sterile dressing and packaged in a sterile packaging, as would be readily understood by those of skill in the art.

In accordance with an embodiment of the present invention, a method of making the wound dressing 10 can include providing a plurality of thermal reflecting domes 14 arranged in an array configuration on a top layer 12 to form a thermal reflective layer 15 (step 100). The thermal reflective layer 15 is combined with a bottom layer 16 formed of a wound contact layer having a wound facing surface 17 to form the wound dressing 10 (step 102). Apexes of each dome of the plurality of thermal reflecting domes 14 are oriented toward the bottom layer 16.

FIG. 1B is a bottom plan view of the wound dressing 10 of FIG. 1, with the bottom layer 16 peeled back halfway to reveal the plurality of thermal reflecting domes 14 of the thermal reflective layer 15. Note that during use, the bottom layer 16 would not be peeled back as shown. This is merely for purposes of illustrating the configuration of the thermal reflective layer 15, and where it is located within the wound dressing 10 construct. In addition to showing the top layer 12, the plurality of thermal reflecting domes 14 of the thermal reflective layer 15, and the bottom layer 16, the present figure also depicts the interstitial gaps 18 disposed between each of the domes of the plurality of thermal reflecting domes 14. As can be seen, in order to place a maximum number of domes into a thermal reflective layer 15, the edges of the domes are in contact with each other and the interstitial gaps 18 are the gaps that result because each of the plurality of thermal reflecting domes 14 have a circular shape. If a lesser quantity of reflective surface is desired for a given dimension of wound dressing 10, then the thermal reflective layer 15 can be constructed such that the plurality of thermal reflecting domes 14 do not make contact with each other, thereby increasing the amount of area attributable to the interstitial gaps 18, as would be appreciated by those of skill in the art. However, the inventor has determined for purposes of providing a maximum amount of thermal reflectivity, it is preferable to have the plurality of thermal reflecting domes 14 in contact, or very close to in contact with each other, or in a honeycomb type of pattern, in the array configuration. If an even lesser amount of interstitial gaps 18 are desired (i.e., if there is less desire for the features provided by such interstitial gaps 18 as described herein), then the plurality of thermal reflecting domes 14 can be configured in staggered rows, where each dome of the plurality of thermal reflecting domes 14 in a first row is in alignment with an intersection or meeting of two domes of the plurality of thermal reflecting domes 14 in an adjacent second row, as would be readily appreciated by those of skill in the art. Likewise, given the present detailed description, those of skill in the art would appreciate other patterns of alignment of the thermal reflecting domes 14 can be implemented to amplify or restrain various performance related variables, such as thermal reflectance, number of thermal reflecting domes 14, size of interstitial gaps 18, etc., such that other configurations can be considered to fall within the scope of the present invention.

Figure 2:
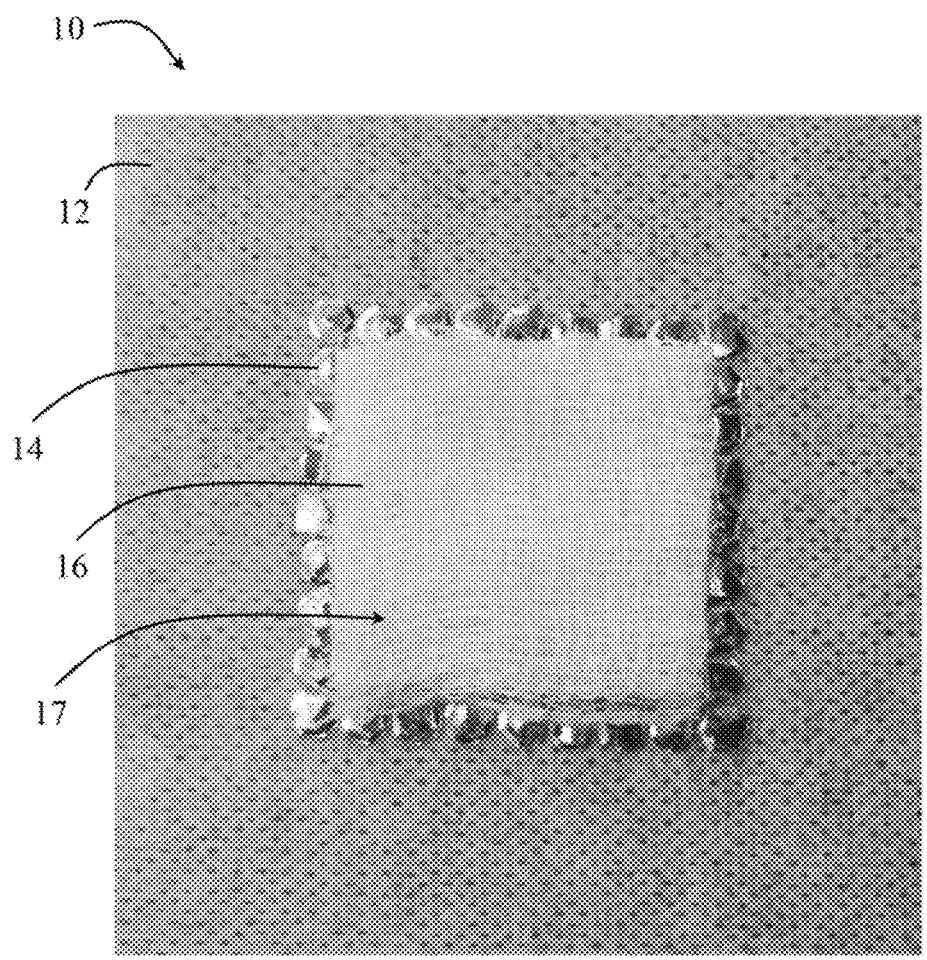
FIG. 2 is a bottom plan view image of the wound dressing, in accordance with aspects of the present invention.

FIG. 2 is a photographic image of the wound dressing 10 of FIG. 1 in accordance with an example embodiment of the present invention. In this image, the top layer 12 is formed of Mefix® self-adhesive fabric, provided by Mölnlycke Health Care. The plurality of thermal reflecting domes 14 are formed of PET with an aluminum vacuum vapor deposition reflective layer disposed thereon. The bottom layer 16 is a conventional gauze.

Figure 3:
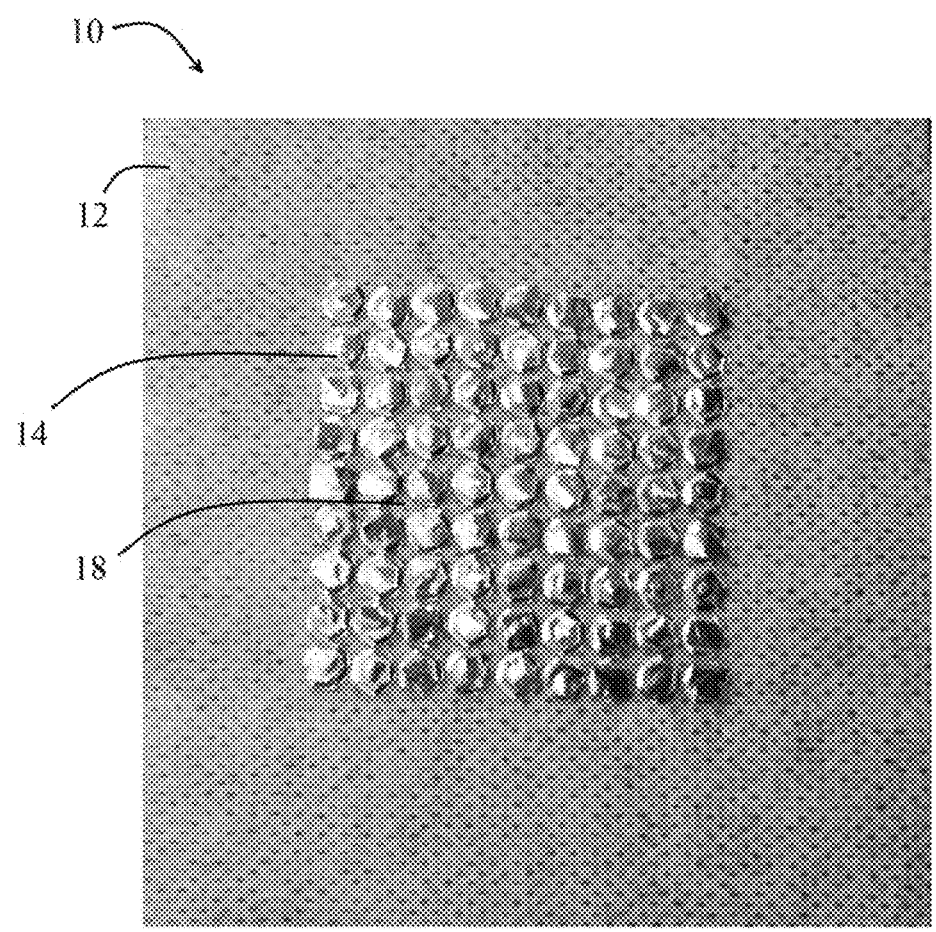
FIG. 3 is a bottom plan view image of a top layer supporting a plurality of thermal reflective domes, in accordance with aspects of the invention.

FIG. 3 depicts a bottom plan view of the wound dressing 10 of FIG. 2, but with the bottom layer 16 gauze removed, so as to clearly show the plurality of thermal reflecting domes 14 in the array configuration. In addition, the interstitial gaps 18 are also clearly depicted in this figure.

Figure 4:
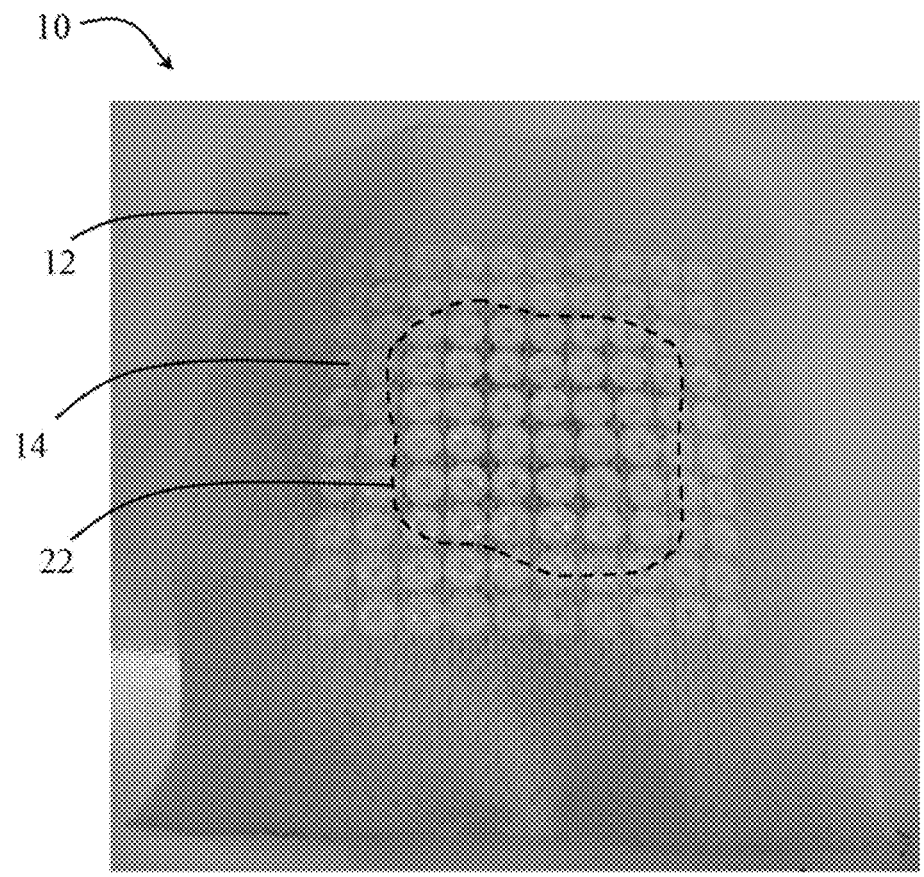
FIG. 4 is a top plan view image of a top layer of the wound dressing, which demonstrates transparency of the top layer enabling visualization of the thermal reflective layer and wound drainage into a bottom layer below the thermal reflective layer.

FIG. 4 depicts a top view of the wound dressing 10 of FIG. 2. The top layer 12 drapes over the wound area including the wound surface 24 and the surrounding periwound skin tissue 26. The flat back portions of each of the plurality of thermal reflecting domes 14 can be seen as a plurality of circular shapes in the array configuration. In addition, this image shows wound exudates 22 seeping through the bottom layer 16 (not viewable in this figure) and depicted with the dotted outline. Thus the wound dressing 10 enables observation of wound exudates 22 that otherwise would not penetrate a thermally reflective wound dressing having, e.g., a solid reflective film layer.

FIG. 5 depicts a side cross-sectional view of the wound dressing 10 in accordance with one embodiment of the present invention. In this instance, there is an additional base layer 20 that supports the plurality of thermal reflecting domes 14 in the array configuration. This embodiment illustrates a separate, stand-alone, thermal reflective layer 15 that does not rely on the top layer 12 to provide the supporting structure for the plurality of thermal reflecting domes 14. Rather, in this configuration, the thermal reflective layer 15 is formed of the base layer 20 and the plurality of thermal reflecting domes 14 to create a stand-alone structure. This stand-alone thermal reflective layer 15 then be incorporated into a conventional wound dressing configuration by placing the stand-alone thermal reflective layer 15 between the top layer 12 and the bottom layer 16 of the wound dressing 10, to achieve the features of the claimed invention.

In operation, the wound dressing 10 with the thermal reflecting domes 14 forming the thermal reflective layer 15 is placed over the wound surface 24 with the bottom layer 16 being placed against the wound surface 24 at the wound facing surface 17. If the wound dressing 10 is of the general nature of a bordered gauze type of wound dressing, then the top layer 12 will include some form of adhesive fabric tape, and the wound dressing 10 can be adhered to the patient's skin at the periwound skin surface 26 (see FIG. 6).

In accordance with an experimental comparison, the present wound dressing 10 was applied to a patient's skin in accordance with the above procedure. Likewise, a conventional bordered gauze (without a thermal reflective layer 15) was applied to a patient's skin in accordance with the same procedure. A temperature probe was placed in the top of the wound bed under the wound dressing 10 in both instances. The conventional bordered gauze went from about 89° F. to 97° F. in 1.8 hours (with measurements taken every 10 seconds). The inventive wound dressing 10 with the thermal reflective layer 15 went from about 89° F. to 97° F. in 0.45 hours. As such, the experiment clearly demonstrated a marked increase in the rate at which the wound returned back to the desired body temperature (or close to the desired body temperature) of 97° F. The inventive wound dressing 10 returned the wound to 97° F. approximately four times faster than the conventional bordered gauze.

As described herein in accordance with the illustrative embodiment(s), the inventive wound dressing 10 is a bordered self-adherent wound care dressing that keeps a wound at or substantially at body temperature to enable the preferred wound healing process. The wound dressing 10 also protects a wound from pathogens entering the wound and it can also absorb wound drainage at the bottom layer 16.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A wound dressing, comprising:
   a top layer;
   a bottom layer on an opposite side of the wound dressing from the top layer, the bottom layer comprised of a wound contact layer having a wound facing surface;
   a thermal reflective layer disposed between the top layer and the bottom layer and comprising a plurality of thermal reflecting domes arranged in an array configuration with apexes of each dome of the plurality of thermal reflecting domes oriented toward the bottom layer of the wound dressing.

2. The wound dressing of claim 1, wherein the thermal reflective layer is passive and does not itself generate heat.

3. The wound dressing of claim 1, wherein each dome of the plurality of thermal reflecting domes has a hemispherical geometry.

4. The wound dressing of claim 1, wherein each dome of the plurality of thermal reflecting domes has a focal length to diameter ratio of between about 0.25 and about 0.5.

5. The wound dressing of claim 1, wherein each dome of the plurality of thermal reflecting domes has a diameter of no greater than about 4 mm.

6. The wound dressing of claim 1, wherein each dome of the plurality of thermal reflecting domes comprises a polymer structure with a reflective coating.

7. The wound dressing of claim 6, wherein the polymer structure comprises a structure of polyethylene terephthalate (PET) or polyvinyl chloride (PVC).

8. The wound dressing of claim 6, wherein the reflective coating comprises a metallic layer.

9. The wound dressing of claim 6, wherein the reflective coating comprises an aluminum vacuum vapor deposition reflective layer.

10. The wound dressing of claim 1, further comprising a plurality of interstitial gaps between each dome of the plurality of thermal reflecting domes.

11. The wound dressing of claim 10, wherein the plurality of interstitial gaps are comprised of needle permeable material.

12. The wound dressing of claim 1, wherein the wound dressing is flexible and compliant to a wound surface upon which it is placed.

13. The wound dressing of claim 1, wherein the bottom layer comprises a gauze, a super-absorbent material, a composite material, or a foam.

14. The wound dressing of claim 1, wherein the top layer comprises an adhesive layer suitable for adhering the wound dressing to a skin surface of a patient.

15. The wound dressing of claim 14, wherein the adhesive layer comprises a tape selected from the group consisting of transparent adhesive film, paper tape, pink tape, fabric tape, and adhesive bandage.

16. The wound dressing of claim 1, wherein the top layer comprises a non-adhesive wrap layer.

17. The wound dressing of claim 1, wherein the plurality of thermal reflecting domes are affixed to the top layer.

18. The wound dressing of claim 1, wherein the plurality of thermal reflecting domes are affixed to a base layer, which is disposed between the top layer and the bottom layer of the wound dressing.

19. A method of making a wound dressing, comprising:
   providing a plurality of thermal reflecting domes arranged in an array configuration on a top layer to form a thermal reflective layer;
   combining the thermal reflective layer with a bottom layer comprising a wound contact layer having a wound facing surface to form the wound dressing, the thermal reflecting domes disposed between the top layer and the bottom layer;
   wherein apexes of each dome of the plurality of thermal reflecting domes are oriented toward the bottom layer.

* * * * *